United States Patent [19]

Durette et al.

[11] Patent Number: 4,894,392

[45] Date of Patent: Jan. 16, 1990

[54] AMINOALKYL NAPHTHALENEDIOLS AS HOST RESISTANCE ENHANCERS

[75] Inventors: Philippe L. Durette, New Providence, N.J.; Timothy F. Gallagher, Harleysville, Pa.

[73] Assignee: Merck & Co., Inc., Rahway, N.J.

[21] Appl. No.: 195,353

[22] Filed: May 12, 1988

Related U.S. Application Data

[60] Division of Ser. No. 90,403, Aug. 27, 1987, abandoned, which is a continuation of Ser. No. 803,036, Nov. 29, 1985, abandoned.

[51] Int. Cl.[4] ..................... A61K 31/35; A61K 31/34; A61K 31/135
[52] U.S. Cl. .................................. 514/459; 514/472; 514/471; 514/655; 549/415; 549/424; 549/425; 549/472; 549/480; 549/492; 564/387
[58] Field of Search ............... 564/387; 514/655, 459, 514/472, 471; 549/492, 415, 424, 472, 480, 425

[56] References Cited

U.S. PATENT DOCUMENTS 3,004,069 10/1961 Duffin ................................ 564/387
3,009,912 11/1961 Duffin ................................ 544/73

FOREIGN PATENT DOCUMENTS 790202 2/1958 United Kingdom .
790203 2/1958 United Kingdom .

OTHER PUBLICATIONS

British Journal of Pharm., vol. 12, pp. 171–175 (1957).
Synthetic Immunostimulants in Antitumor Therapy–Drugs of the Future, vol. 8, pp. 615–638 (1983).
Immunomodulators in the Immunotherapy of Cancer and Other Diseases–Trends in Pharmacological Sciences (TIPS), pp. 191–194 (1982).
The Experimental and Clinical Use of Immunomodulating Drugs in the Prophylaxis and Treatment of Infections–Infection, vol. 12, p. 1957 (1984).

Primary Examiner—Nicky Chan

[57] ABSTRACT

Disclosed are specific aminoalkyl naphthalenediol derivatives that enhance host resistance to infectious organisms. Such agents are administered prophylactically to individuals whose resistance to infection is comprised by chemotherapy, surgery, burns or other forms of severe stress.

4 Claims, No Drawings

AMINOALKYL NAPHTHALENEDIOLS AS HOST RESISTANCE ENHANCERS

This is a division of application Ser. No. 090,403 filed Aug. 27, 1987 which is a continuation of application Ser. No. 803,036 filed Nov. 29, 1985 both abandoned.

BACKGROUND OF THE INVENTION

1. Field of the Invention

The present invention relates to certain aminoalkyl naphthalenediol derivatives that enhance host resistance to infectious organisms which are administered prophylactically to individuals whose resistance to infections is compromised by chemotherapy, surgery, burns or other forms of severe stress.

2. Brief Description of Disclosures in the Art

Recent medical progress has resulted in beneficial therapy for many patients with conditions which were previously untreatable. As a result of both the extended survival of such patients and the therapeutic methods employed, today's physicians are more frequently encountering the patient who is at great risk of developing infection because his host defenses have been impaired. For example, infection is now the leading cause of death in both leukemia and lymphoma. Interference with host defense mechanisms has resulted in the frequent development of infections in this type of patient with organisms formerly considered nonpathogenic.

Over the past few decades, the host defense system has undergone intensive study, and it has become clear that this system involves several different but interacting resistance mechanisms. In addition, the ability to defend oneself against a specific pathogen can frequently be ascribed to a particular mechanism. Therefore, patients with discrete immunologic defects are frequently at risk for infection with a relatively limited number of pathogens. On the other hand, those with extensive host defense system dysfunction involving several different defense mechanisms, as might occur during intensive therapy of malignant diseases, are often at risk for infections with a bewildering array of potential pathogens. Since fairly specific and effective therapies are available for most of the pathogens encountered in this setting, the establishment of an etiologic diagnosis and beginning of the appropriate therapy of infection early are of utmost importance in the management of these patients.

It has been found that certain compounds including lipopolysaccharide, glucans, ubiquinones, bestatin, amphotericin B, tuftsin, thymic hormones, interferon, polyadenylic acid complexes, pyran copolymers, levamisole, methisoprinol and the like, although not specifically therapeutic for a particular pathogen, act in such a manner to improve the host resistance to infection by bacteria, virus, fungus, or parasite in a human host whose immunological system has been compromised.

In the past, bacterial cell wall products (e.g., BCG, C. parvum, etc.), as well as plant polysaccharides (e.g., lentinan, krestin, etc.), have been employed to stimulate the natural host resistance. These agents all suffer from undesirable toxic side effects, such as granulomatous inflammation, etc. Presumably the development of inflammation enhances the mobilization and activation of inflammatory cells as well as augmentation of the immune response (adjuvant effect).

In light of the above discussion, new classes of organic compounds are constantly being evaluated and screened to see if they possess host resistance enhancement activity.

One class of compounds recently of interest are the aminoalkyl naphthalenediols.

In the art, naphthalenediols are described in U.S. Pat. No. 3,009,912; British Pat. Nos. 790,203; 790,202; and in Brit. J. Pharmacol. 12(1957) p. 171, "Anti-Malarial Activity of Hydroxy-Substituted Naphthalene Compounds" by W. M. Duffin and I. M. Rollo. The above compounds are described as being active as antimalarial agents against blood forms of plasmodium species. However, there is no specific suggestion as to their use as host resistance enhancement agents.

At present, there is no effective host resistance enhancer on the market that does not possess the ability to cause intense granulomatous inflammation. The use of host resistance compounds that cause inflammation is not desirable.

For reviews, see (1) J. Kralovec, "Synthetic Immunostimulants in Antitumor Therapy," *Drugs of the Future* 8(1983)615; (2) J. W. Hadden, "Immunomodulators in the Immunotherapy of Cancer and Other Diseases," *Trends in Pharmacological Sciences*, (1982)191; (3) E. Arrigoni-Martelli, "Developments in Drugs Enhancing the Immune Response," *Meth. Find. Exptl. Clin. Pharmacol*, 3(1981)247; and (4) J. Drews, "The Experimental and Clinical Use of Immunomodulating Drugs in the Prophylaxis and Treatment of Infections," *Infection*, 12(1984)157.

Therefore, it is an object of this invention to provide host resistance enhancement agents that are safe, effective and whose therapeutic mechanism does not involve significant granulomatous inflammation.

Further, it is an object of this invention to provide a pharmaceutical composition for host resistance enhancement including said agent and an acceptable pharmaceutical carrier thereof.

Furthermore, it is also an object of this invention to provide a method of treatment for enhancing host resistance in humans who are immunologically compromised.

SUMMARY OF THE INVENTION

It has been found that certain aminoalkyl naphthalenediol derivatives do in fact possess excellent activity as host resistance enhancing agents without causing significant granulomatous inflammation as a side effect. Further, the advantages are that the said compounds are non-pyrogenic and they do not sensitize the host to endotoxin.

By this invention there is provided a compound of the formula:

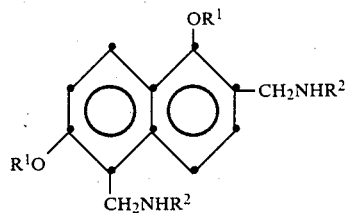

where $R^1$ is independently selected from H, $C_1$–$C_6$ alkyl; $R^2$ is independently selected from substituted monocycloalkyl or unsubstituted or substituted di- or tri- cycloalkyl, or heterocycloalkyl, or pharmaceutically acceptable acid addition salts thereof.

Further provided is a pharmaceutical composition comprising a compound of the above formula and a pharmaceutically acceptable carrier.

Also provided is a method for improving the host resistance in a subject who is immunologically compromised, comprising administering to said subject the above-described pharmaceutical composition containing a host resistance enhancing agent.

DETAILED DESCRIPTION OF THE INVENTION AND PREFERRED EMBODIMENTS

The compounds of the present invention may be prepared by reacting the appropriate naphthalenediol with formaldehyde and the appropriate amine, $R^2NH_2$, in a suitable solvent such as methanol; the reagents will react on standing or may be heated together. The product of this reaction is a bis-oxazine compound. A 1,3-oxazine ring is formed on each side of the naphthalene ring by condensation of the naphthalenediol with 4 molar equivalents of formaldehyde in the presence of two equivalents of $R^2NH_2$:

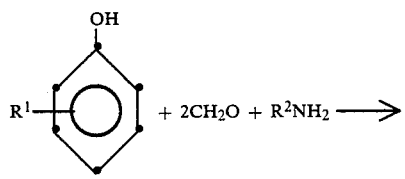

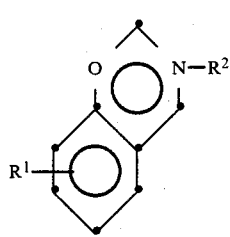

The oxazine rings can be opened by acid hydrolytic methods and the formaldehyde removed in a manner to be described below.

As an example, the following sequence of formulae illustrates the preparation of the compound 2,5-bis(-trans-4-methylcyclohexylaminomethyl)-naphthalene-1,6-diol, which is a preferred compound:

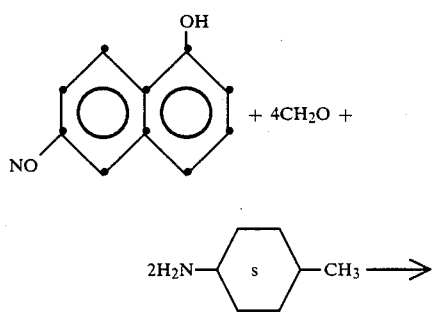

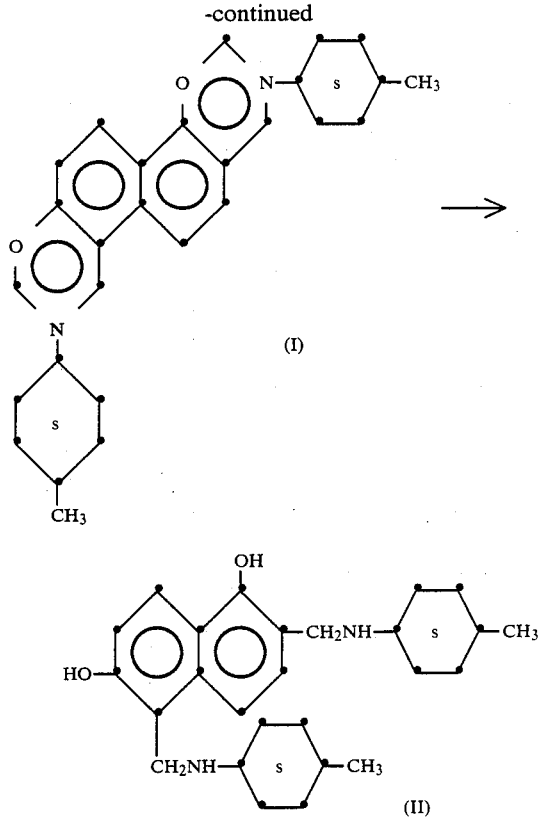

The opening of the oxazine rings in a compound of the type in Formula I, resulting in a compound of Formula II, may be carried out by treating I with an acid in an aqueous alcohol system, such as aqueous ethanol or aqueous isopropanol. For this purpose, 10% hydrochloric acid or 2N sulphuric acid are convenient. The reaction may also be carried out in the cold in the presence of a compound such as 2,4-dinitrophenylhydrazine which will react with formaldehyde as it is formed; this prevents loss of material due to polymerization.

Preparation of the 1,6-dialkoxy compounds, which include alkoxy groups of $C_1$ to $C_6$ alkyl, which can be linear or branched, generally involves dissolving the 1,6-dihydroxy compound, wherein the amino functionalities are protected, such as their benzylcarbamates, in a suitable solvent such as tetrahydrofuran, 1,4-dioxane, N,N-dimethylformamide, dimethylsulfoxide, hexamethylphosphorictriamide, or the like, adding base such as sodium hydride, or the like, to create the phenoxide salt and adding a suitable alkylating agent such as iodomethane, bromoethane, or the like, in sufficient quantity being at least 2 molar equivalents such that the dialkoxy compound in the 1,6-positions is formed, removal of the amino protecting groups, such as by hydrogenolysis, and, finally, generation of the bis hydrochloride salt by treatment with aqueous HCl.

Representative classes of $R^2$ groups are chosen from cycloaliphatic, heterocycloaliphatic and their $C_1$–$C_6$ alkoxy derivatives.

Representative examples of $R^2$ include 1-adamantyl, 2-adamantyl, 3-methyl-1-adamantyl, 3-methyl-2-adamantyl, 3,5-dimethyl-1-adamantyl, 3,5-dimethyl-2-adamantyl, 3-ethyl-1-adamantyl, 3-ethyl-2-adamantyl, 3-propyl-1-adamantyl, 3-propyl5-ethyl-adamantyl, 3-t- butyl-2-adamantyl, 3-isopropyl-1-adamantyl, 3-methoxy-1-adamantyl, 3-ethoxy-1-adamantyl, 3-propoxy-1-adamantyl, 1-adamantylmethyl, 2-adamantylmethyl, 3-methyl-1-adamantylmethyl, 3-methyl-2-adamantylmethyl, 3,5-dimethyl-1-adamantylmethyl-, 3-ethyl-1-adamantylmethyl-, 3-propyl-1-adamantylmethyl, 3,5-dimethyl-2-adamantyl, 3-methoxy-1-adamantylmethyl, 3-ethoxy-1-adamantylmethyl, 3-ethyl-5-methoxy-1-adamantyl, cyclohexyl, 2-,3-, or 4-monomethylcyclohexyl (both cis & trans-isomers), 2,4-dimethylcyclohexyl, 2,4,6-trimethylcyclohexyl, 4-t-butyl, 2-propylcyclohexyl, 3-propylcyclohexyl, 4-propylcyclohexyl, 4-t-butylcyclohexyl, 4-secbutylcyclohexyl, 2,3, or 4-methoxycyclohexyl, 4-ethoxycyclohexyl, 4-propoxycyclohexyl, 4-butoxycyclohexyl, cyclohexylme.thyl-, 2-,3-,4-trimethylcyclohexylmethyl-, 2,4-dimethylcyclohexylmethyl-, 2-methoxycyclohexylmethyl-, 4-t-butoxycyclohexylmethyl-, 3-isopropoxycyclohexylmethyl-, 4-tetrahydropyranyl-, 3-tetrahydropyranyl, 2-tetrahydropyranyl, 2-methyl-4-tetrahydropyranyl, 3-methyl-4-tetrahydropyranyl, 2,5-dimethyltetrahydro-4-pyranyl, 2-methoxy-tetrahydro-4-pyranyl, 2,6-dimethoxytetrahydro-4-pyranyl, tetrahydropyranyl-4-methyl, 2-methyltetrahydropyranyl-4-methyl, 2,5-dimethoxytetrahydropyranyl-4-methyl; cyclopentyl, cyclopentylmethyl or substituted cyclopentyl, similarly as with cyclohexyl; cycloheptyl or substituted cycloheptyl, similarly as with cyclohexyl; exo or endo-norbornyl, tetrahydrofurfuryl, and the like, and cis and trans isomers thereof.

Utilizing amine with the above described R² radicals for synthesis of the subject compounds and their oxazines, the compounds listed in the following table were synthesized.

TABLE

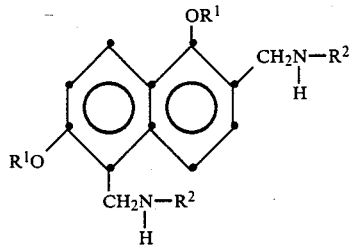

| Compound | R¹ | R² |
|---|---|---|
| 1 | H | 1-Adamantyl |
| 2 | H | 2-Adamantyl |
| 3 | H | cyclohexylmethyl |
| 4 | H | exo-2-norbornyl |
| 5 | H | 4-tert-butylcyclohexyl (cis and trans) |
| 6 | H | tetrahydrofurfuryl |
| 7 | H | 2-methylcyclohexyl |
| 8 | H | 3-methylcyclohexyl |
| 9 | H | 4-methylcyclohexyl (cis) |
| 10 | H | 4-methylcyclohexyl (trans) |
| 11 | H | cyclopentylmethyl |
| 12 | H | 4-methoxycyclohexyl |
| 13 | H | 2-methylcyclopentyl (trans) |
| 14 | H | tetrahydro-4H—pyran-4-yl |
| 15 | CH₃ | cyclohexyl |
| 16 | (CH₂)₃CH₃ | cyclohexyl |

The compound in the present invention possess immunostimulatory properties and may be used as immunological adjuvants to stimulate the host immune response. They are especially useful for increasing the antigenicity of weakly immunogenic agents in vaccines against bacterial, viral, or parasitic infections or against various tissue antigens of normal or pathogenic origin. They can be used in place of whole killed mycobacterial cells in *Freund's Complete Adjuvant*. In addition, the compounds of the present invention when incorporated into a vaccine either as an aqueous or oil formulation lack the deleterious side effects observed in vaccine compositions containing Freund's Complete Adjuvant. Furthermore, the compounds of the present invention by themselves provide non-specific host protection against infectious organisms, for example, *Klebsiella pneumoniae, Candida albicans, Staphylococcus aureus* and *Pseudomonas aeruginosa.* They are also capable of potentiating antibiotic activity.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of Formula II. Among the pharmaceutical preparations relevant to this invention are salts that are administered by external route, for example, orally, rectally or parenterally to mammalian species. Preparations may be administered that contain the pharmacologically active compound by itself or mixed with a pharmacolbgically acceptable carrier. The dose of the pharmacologically active compound depends on the animal specie, the age, and the state of the individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by bacteria, viruses or pathogenic parasites, owing to immunity by humoral antibodies and/or to cellular mediation.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immunedeficiency, but also acquired general deficiency (i.e., not antigen-specific) as appears with age, during initial shock from a grave illness, and before and soon after radiation therapy or immunosuppressive hormones. The said compounds can subsequently be administered in combination with anti-infectious antibiotics, chemical therapeutics or other methods of treatment, to combat immunological deficiencies. The described compounds are thus indicated equally for general prophylaxis of infectious disease in man and animal.

EXAMPLE 1

1,6-Dihydroxy-2,5-bis-(1-adamantanaminomethyl)-naphthalene dihydrochloride

Step A: 2:9-di-(1-Adamantyl)-1:2:3:4:7:8:9:10-octahydro-2:9-diaza-4:7-dioxachrysene To a mixture of 1-adamantanamine (7.6 g, 0.050 mol) and methanol (40 ml) cooled in an ice-bath were added with stirring 37% formaldehyde (wt. % solution in water, 8.1 ml, 0.10 mol) followed by a solution of 1,6-dihydroxynaphthalene (4.0 g, 0.025 mol) in methanol (25 ml). The reaction mixture was allowed to attain room temperature and was stirred overnight. The resulting solid was filtered and washed with methanol. Purification was achieved by vacuum filtration through a pad of silica gel (Merck β 7734) and elution initially with dichloromethane and subsequently 100:1 and 25:1 dichloromethane-diethyl ether; yield 6.8 g (53%); m/z (e.i.) 347 (M-163). The 90 MHz NMR spectrum in chloroform-d was in accord with the desired structure: δ 4.17 (s, 2H, CH$_2$N); 4.34 (s, 2H, CH$_2$N); 5.02 (s, 2H, OCH$_2$N); and 5.12 (s, 2H, OCH$_2$N).

Step B: 1,6-Dihydroxy-2,5-bis-(2-adamantanaminomethyl) naphthalene dihydrochloride A mixture of 2:9-di-(1-adamantyl)-1:2:3:4:7:8:9:10-octahydro-2:9-diaza-4:7-dioxachrysene (4.5 g, 8.8 mmol), concentrated hydrochloric acid (50 ml) and 50% ethanol (1.6 L) was heated at reflux temperature for 48 hours, cooled, and evaporated under diminished pressure. The residue was triturated with isopropanol and diethyl ether to afford a solid that was filtered and recrystallized from 80% ethanol-diethyl ether; yield 3.0 g (61%); mass spectrum (fast atom bombardment): m/z 486 (free base). The 200 MHz NMR spectrum in methanol-d$_4$ was in accord with the desired structure: δ 4.38 (s, 2H, CH$_2$N); 4.65 (s, 2H, CH$_2$N); 7.29 (d, 1H, phenyl); 7.59 (m, 2H, phenyl); and 8.32 (d, 1H, phenyl).

EXAMPLE 2

1,6-Dihydroxy-2,5-bis-(cyclohexylmethylaminomethyl)-naphthalene dihydrochloride

Step A: 2:9-di-(Cyclohexylmethyl)-1:2:3:4:7:8:9:10-octahydro-2:9-diaza-4:7-dioxachrysene Employing the procedure described in Step A of Example 1, but substituting for the 1-adamantanamine an equivalent amount of cyclohexylmethylamine, the product was obtained as a white solid after recrystallization from 1,4-dioxane. The 200 MHz NMR spectrum in chloroform-d was in accord with the desired structure: δ 2.60 (d, 4H,

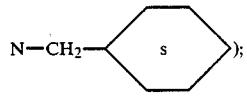

4.06 (s, 2H, CH$_2$N); 4.26 (s, 2H, CH$_2$N); 4.90 (s, 2H, OCH$_2$N); 5.00 (s, 2H, OCH$_2$N); 7.00 (d, 1H, phenyl); 7.10 (dd, 2H, phenyl); and 7.97 (d, 1H, phenyl).

Step B: 1,6-Dihydroxy-2,5-bis-(cyclohexylmethylaminomethyl)-naphthalene dihydrochloride A mixture of 2:9-di-(cyclohexylmethyl)-1:2:3:4:7:8:9:10-octahydro-2:9-diaza-4:7-dioxachrysene (500 mg, 1.15 mmol), concentrated hydrochloric acid (2.55 ml) and 80% ethanol (50 ml) was heated at reflux temperature for 3 hours, cooled, and evaporated under diminished pressure. The residue was triturated with isopropanol-diethyl ether to give a solid that was filtered and recrystallized from 80% ethanol-diethyl ether; yield 210 mg (38%); mass spectrum (fast atom bombardment): m/z 411 (M). The 200 MHz NMR spectrum in methanol-d$_4$ was in accord with the desired structure: δ 2.93 (d, 2H,

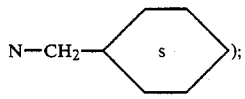

2.98 (d, 2H,

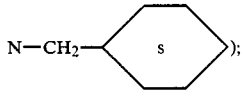

4.42 (s, 2H, CH$_2$N); and 4.70 (s, 2H, CH$_2$N).

EXAMPLE 3

1,6-Dihydroxy-2,5-bis-(4-tert-butylcyclohexylaminomethyl)-naphthalene dihydrochloride (mixture of isomers)

Step A: 2:9-di-(4-tert-Butylcyclohexyl)-1:2:3:4:7:8:9:10-octahydro-2:9-diaza-4:7-dioxachrysene To a mixture of 4-tert-butylcyclohexylamine (mixture of isomers) (9.7 g, 0.062 mol) and methanol (35 ml) cooled in ice bath were added with stirring 37% formaldehyde (wt. % solution in water, 10.0 ml, 0.12 mol) and subsequently a solution of 1,6-dihydroxynaphthalene (5.0 g, 0.031 mol) in methanol (25 ml). The bath was removed and the mixture was heated at reflux temperature for 1 hour and cooled. The solid product was filtered and washed with eethanol and diethyl ether. The solid was dissolved in the minimal amount of dichloromethane and vacuum filtered through a pad of silica gel (Merck β 7734) and elution with 10:1 dichloromethane-diethyl ether. Thin layer chromatographic (tlc) investigation (1:1 hexane-diethyl ether) indicated isolation of a two-component mixture which was subjected to flash column chromatography on silica gel (elution with 10:1 hexane-diethyl ether). 90 MHz NMR spectral investigation (chloroform-d) of the thin layer more mobile product (1.2 g) indicated a mixture of isomers, whereas the less mobile product (1.3 g) to be a single isomer: 0.80 (s, 18H, 2×C(CH$_3$)$_3$); δ 4.19 (s, 2H, CH$_2$N); 4.38 (s, 2H, CH$_2$N); 5.08 (s, 2H, OCH$_2$N); and 5.16 (s, 2H, OCH$_2$N).

Step B: 1,6-Dihydroxy-2,5-bis-(4-tert-butylcyclohexylaminomethyl)-naphthalene dihydrochloride (mixture of isomers)

A mixture of the faster-moving product from Step A above (1.0 g) and concentrated hydrochloric acid (2.5 ml) in 80% ethanol (100 ml) was heated at reflux temperature for 18 hours, cooled, and evaporated under diminished pressure. The residue was triturated with isopropanol-diethyl ether, and the resulting solid filtered, washed with ether, and dried in vacuo to give the product as a light tan solid; yield 0.95 g (87%). The 200 MHz NMR spectrum in methanol-d$_4$ indicated a mixture of isomers.

EXAMPLE 4

1,6-Dihydroxy-2,5-bis-(4-tert-butylcyclohexylaminomethyl)-naphthalene dihydrochloride (single isomer)

The slower-moving product from Step A of Example 3 (1.0 g) was treated with concentrated hydrochloric acid in aqueous ethanol and worked-up in a similar manner as that described in Step B of Example 3 to give the product as a white solid (300 mg), whose 200 MHz NMR spectrum in methanol-d$_4$ indicated a single isomer: $\delta$ 0.91 (s, 18H, 2×C(CH$_3$)$_3$); 4.43 (s, 2H, CH$_2$N); 4.70 (s, 2H, CH$_2$N); 7.31 (d, 1H phenyl); 7.62 (dd, 2H, phenyl); and 8.33 (d, 1H phenyl).

EXAMPLE 5

1,6-Dihydroxy-2,5-bis-(2-methylcyclohexylaminomethyl)-naphthalene dihydrochloride (mixture of isomers)

Step A: 2:9-di-(2-Methylcyclohexyl)-1:2:3:4:7:8:9:10-octahydro-2:9-diaza-4:7-dioxachrysene Employing the procedure described in Step A of Example 1, but substituting for the 1-adamantanamine an equivalent amount of 2-methylcyclohexylamine (mixture of cis, trans isomers) and carrying out the reaction at room temperature for 18 hours, the title compound was obtained as an isomeric mixture that solidified upon trituration with hexane.

Step B: 1,6-Dihydroxy-2,5-bis-(2-methylcyclohexylaminomethyl)-naphthalene dihydrochloride (mixture of isomers)

A mixture of 2:9-di-(2-methylcyclohexyl)-1:2:3:4:7:8:9:10-octahydro-2:9-diaza-4:7-dioxachrysene (0.80 g) and concentrated hydrochloric acid (2.5 ml) in 80% ethanol (50 ml) was heated at reflux temperature for 18 hours, cooled, and evaporated. The resulting solid was recrystallized from 80% ethanol-diethyl ether to afford the product (200 mg) as a mixture of cis, trans isomers (as indicated by the 200 MHz NMR spectrum in methanol-d$_4$); mass spectrum (fast atom bombardment): m/z 411 (M+H). N.m.r. data: $\delta$ 1.16 (d, 6H, 2×CH$_3$); 4.44 (m, 2H, CH$_2$N); and 4.70 (s, 2H, CH$_2$N).

EXAMPLE 6

1,6-Dihydroxy-2,5-bis-(3-methylcyclohexylaminomethyl)-naphthalene dihydrochloride (mixture of isomers)

Employing the procedure described in Example 5, but substituting for the 2-methylcyclohexylamine used in Step A thereof, an equivalent amount of 3-methylcyclohexylamine (mixture of cis, trans isomers), there were prepared in sequence:

Step A: 2:9-di-(3-Methylcyclohexyl)-1:2:3:4:7:8:9:10-octahydro-2:9-diaza-4:7-dioxachrysene The product was purified by chromatography on a pad of silica gel (Merck $\beta$ 7734, packed as a slurry in 10:1 hexane-ether) and elution with 10:1 hexane-ether.

Step B: 1,6-Dihydroxy-2,5-bis-(3-methylcyclohexylaminomethyl)-naphthalene dihydrochloride Obtained as a mixture of isomers as indicated by the 200 MHz NMR spectrum in methanol-d$_4$: $\delta$ 1.01 (d, 3H, CH$_3$-minor isomer); 1.02 (d, 3H, CH$_3$-major isomer); 4.42 (s, 2H, CH$_2$—N); and 4.68 (s, 2H, CH$_2$N).

EXAMPLE 7

1,6-Dihydroxy-2,5-bis-(trans-4-methylcyclohexylaminomethyl)-naphthalene dihydrochloride Step A: 2:9-di-(trans-4-Methylcyclohexyl)-1:2:3:4:7:8:9:10-octahydro-2:9 diaza-4:7-dioxachrysene Starting from 1,6-dihydroxynaphthalene (10.0 g, 0.062 mol) and 4-methylcyclohexylamine (mixture of cis and trans isomers) (14.1 g, 0.124 mol), and following the procedure set forth in Step A of Example 1, initially an isomeric mixture (6.7 g) was obtained after vacuum filtration through a pad of silica gel (Merck $\beta$ 7734) and elution with 50:1 dichloromethane-diethyl ether. This mixture (5.7 g) was further chromatographed on a Waters Prep LC/system 500 using dual Prep-PAK ™ 500 silica columns with 5:1 hexane-ethyl acetate as the eluant. Two main fractions were collected; that containing the slower-moving component (2.5 g) was identified on the basis of its 200 MHz NMR spectrum in chloroform-d as the pure trans isomer: $\delta$ 0.84 (d, 6H, 2CH$_3$'S); 4.18 (s, 2H, CH$_2$N) 4.38 (s, 2H, CH$_2$N); 5.05 (s, 2H, OCH$_2$N); 5.16 (s, 2H, OCH$_2$N); 6.98 (d, 1H, phenyl); 7.14 (dd, 2H, phenyl); and 7.96 (d, 1H, phenyl).

Step B: 1,6-Dihydroxy-2,5-bis-(trans-4-methylcyclohexylaminomethyl)-naphthalene dihydrochloride The trans isomer from Step A above (500 mg) was treated with concentrated hydrochloric acid (1 ml) in 80% ethanol (30 ml) for 24 hours at reflux temperature, cooled, and evaporated. The solid was triturated with isopropanol, filtered, washed with isopropanol and diethyl ether and dried in vacuo; yield 475 mg (85%). The 200 MHz NMR spectrum in methanol-d$_4$ was in accord with the desired structure; $\delta$ 0.94 (d, 3H, CH$_3$); 0.95 (d, 3H, CH$_3$); 4.43 (s, 2H, CH$_2$N); 4.69 (s, 2H, CH$_2$N); 7.31 (d, 1H, phenyl); 7.62 (dd, 2H, phenyl); and 8.32 (d, 1H, phenyl); mass spectrum (fast atom bombardment): m/z 411 (M+H).

EXAMPLE 8

1,6-Dihydroxy-2,5-bis-(4-methoxycyclohexylaminomethyl)-naphthalene dihydrochloride (mixture of isomers)

Employing the procedure described in Example 5, but substituting for the 2-methylcyclohexylamine used in Step A thereof, an equivalent amount of 4-methoxycyclohexylamine (mixture of cis and trans isomers), there were prepared in sequence:

Step A: 2:9-di-(4-Methoxycyclohexyl)-1:2:3:4:7:8:9:10-octahydro-2:9-diaza-4:7-dioxachrysene;

Step B: 1,6-Dihydroxy-2,5-bis-(4-methoxycyclohexylaminomethyl)-naphthalene dihydrochloride (mixture of isomers)-the 200 MHz NMR spectrum in methanol-d$_4$ indicated a mixture of cis and trans isomers

EXAMPLE 9

1,6-Dihydroxy-2,5-bis-(4-oxa-cyclohexylaminomethyl) naphthalene dihydrochloride Employing the procedure described in Example 5, but substituting for the 2-methylcyclohexylamine used in Step A thereof, an equivalent amount of 4-oxacyclohexylamine, there were prepared in sequence:

Step A: 2:9-di-(4-Oxa-cyclohexyl)-1:2:3:4:7:8:9:10-octahydro-2:9-diaza-4:7-dioxachrysene; n.m.r. data (200 MHz, CDCl$_3$): δ 4.20 (s, 2H, CH$_2$N); 4.40 (s, 2H, CH$_2$N); 5.08 (s, 2H, OCH$_2$N); 5.18 (s, 2H, OCH$_2$N); 6.99 (d, 1H, phenyl); 7.14 (dd, 2H, phenyl); and 7.96 (d, 1H, phenyl; mass spectrum (e.i.): m/z 410 (M).

Step B: 1,6-Dihydroxy-2,5-bis-(4-oxa-cyclohexylaminomethyl)-naphthalene dihydrochloride-the 200 MHz NMR spectrum in methanol-d$_4$ was in accord with the desired structure

EXAMPLE 10

1,6-Dimethoxy-2,5-bis-(cyclohexylaminomethyl)-naphthalene dihydrochloride

Step A: 1,6-Dihydroxy-2,5-bis-(cyclohexylaminomethyl)-naphthalene

To a solution of 1,6-dihydroxy-2,5-bis-(cyclohexylaminomethyl)-naphthalene dihydrochloride (prepared by modification of the process set forth in U.S. Pat. No. 3,009,912) (5.0 g, 0.011 mol) in water (200 ml) was added 0.1N sodium hydroxide (220 ml, 0.022 mol). The solid that separated out was collected by filtration, washed with water, and dried in vacuo; yield 4.0 g (95%). The 200 MHz NMR spectrum in chloroform-d was in accord with the desired structure. Mass spectrum(fast atom bombardment): m/z 383 (M+H).

Step B: 1,6-Di-benzyloxycarbonyloxy-2,5-bis-[N-(cyclohexyl)-benzyloxycarbonylaminomethyl]naphthalene To a solution of 1,6-dihydroxy-2,5-bis-(cyclohexylaminomethyl)-naphthalene (3.8 g, 9.9 mmol) in dichloromethane (100 ml) were added, with cooling in an ice bath, triethylamine (6.9 ml, 50 mmol) and dropwise with stirring benzyl chloroformate (5.6 ml, 40 mmol). The reaction mixture was stirred at room temperature for 1 hour, diluted with ether, washed three times with water, dried (sodium sulfate) and evaporated to give the product as a thick syrup; yield 2.0 g.

Step C: 1,6-Dihydroxy-2,5-bis-[N-(cyclohexyl)-benzyloxycarbonylaminomethyl)-naphthalene A solution of the crude product from Step B (2.0 g, 2.3 mmol) in methanol (50 ml) was treated with sodium methoxide (120 mg, 2.2 mmol) for 18 hours at room temperature. The mixture was evaporated, the residue taken up in diethyl ether, acetic acid (1 ml) added, the solution washed three times with water, saturated acueous sodium chloride solution, dried (sodium sulfate) and evaporated. The crude product was vacuum filtered through a column of silica gel (Merck β 7734) eluted with 2:1 hexane-ether; yield 1.5 g.

Step D: 1,6-Dimethoxy-2,5-bis-[N-(cyclohexyl)benzyloxycarbonylaminomethyl)-naphthalene To a suspension of sodium hydride (97%) (110 mg) in N,N-dimethylformamide (5 ml) was added dropwise under a nitrogen atmosphere a solution of 1,6-dihydroxy-2,5-bis-[N-(cyclohexyl)-benzyloxycarbonylaminomethyl)-naphthalene (1.0 g, 1.5 mmol) in N,N-dimethylformamide (5 ml). The reaction mixture was stirred at room temperature for 1 hour, at which time iodomethane (0.37 ml, 6.0 mmol) was added. The mixture was stirred at room temperature for an additional hour, poured into water, and extracted with diethyl ether. The combined extracts were washed three times with water, saturated aqueous sodium chloride solution, dried (sodium sulfate) and evaporated. The crude product was chromatographed on a column of silica gel (Merck β 7734) that was eluted with dichloromethane. Fractions containing pure product were combined and evaporated to afford 1,6-dimethoxy-2,5-bis-[N-(cyclohexyl)-benzyloxycarbonylaminomethyl)-naphthalene; yield 360 mg (35%).

Step E: 1,6-Dimethoxy-2,5-bis-(cyclohexylaminomethyl)-naphthalene

A solution of 1,6-dimethoxy-2,5-bis-[N-(cyclohexyl)-benzyloxycarbonylaminomethyl)-naphthalene (250 mg) in methanol (10 ml) was hydrogenated at atmospheric pressure in the presence of 5% palladium -on- charcoal (50 mg) for 2 hours at room temperature. The catalyst was removed by filtration through Celite, and the filtrate was evaporated to afford the product as a yellow syrup; yield 60 mg (37%).

Step F: 1,6-Dimethoxy-2,5-bis-(cyclohexylaminomethyl)-naphthalene dihydrochloride To a solution of the free base (60 mg) in methanol (5 ml) was added a drop of concentrated hydrochloric acid. Ether was added until the product separated out as an oil. The mixture was evaporated and triturated with isopropanol and ether. The solid was filtered, washed with ether, and dried in vacuo; yield 50 mg (72%). The 200 MHz NMR spectrum in methanol-d$_4$ was in accord with the desired structure: δ 4.06 (s, 3H, OCH$_3$); 4.14 (s, 3H, OCH$_3$); 4.44 (s, 2H, CH$_2$N); 4.74 (s, 2H, CH$_2$N); 7.70 (dd, 2H, phenyl); 8.02 (d, 1H, phenyl); and 8.40 (d, 1H, phenyl).

EXAMPLE 11

1,6-Di-(n-butyloxy)-2,5-bis-(cyclohexylaminomethyl)-naphthalene dihydrochloride Employing the procedure described in Example 10, but substituting for the iodomethane used in Step D thereof, an equivalent amount of 1-iodobutane, there were prepared in sequence:

1,6-Di-(n-butyloxy)-2,5-bis-[N-(cyclohexyl)-benzyloxycarbonylaminomethyl)-naphthalene 1,6-Di-(n-butyloxy)-2,5-bis-(cyclohexylaminomethyl) naphthalene 1,6-Di-(n-butyloxy)-2,5-bis-(cyclohexylaminomethyl) naphthalene dihydrochloride; n.m.r. data (200 MHz, CD$_3$OD); 4.10 (t, 2H, OCH$_2$); 4.36 (t, 2H, OCH$_2$); 4.44 (s, 2H, CH$_2$N); 4.74 (s, 2H, CH$_2$N); 7.64 (d, 1H, phenyl); 7.75 (d, 1H, phenyl); 8.02 (d, 1H, phenyl); and 8.36 (d, 1H, phenyl).

EXAMPLE 12

1,6-Dihydroxy-2,5-bis-(cyclopentylmethylaminomethyl)-naphthalene dihydrochloride Employing the procedure described in Example 5, but substituting for the 2-methylcyclohexylamine used in Step A thereof, an equivalent amount of aminomethylcyclopentane, there were prepared in sequence:

Step A: 2:9-di-(Cyclopentylmethyl)-1:2:3:4:7:8:9:10-octahydro-2:9-diaza-4:7-dioxachrysene Step B: 1,6-Dihydroxy-2,5-bis-(cyclopentylmethylaminomethyl)-naphthalene dihydrochloride

EXAMPLE 13

1,6-Dihydroxy-2,5-bis-(trans-2-methylcyclopentylaminomethyl)-naphthalene dihydrochloride Employing the procedure described in Example 5, but substituting for the 2-methylcyclohexylamine used in Step A thereof, an equivalent amount of trans-2-methylcyclopentylamine, there were prepared in sequence:

Step A: 2:9-di-(trans-2-methylcyclopentyl)-1:2:3:4:7:9:10-octahydro-2:9-diaza-4:7-dioxachrysene; n.m.r. data (200 MHz, CDCl$_3$): δ 0.95 (d, 3H, CH$_3$); 0.97 (d, 3H, CH$_3$); 5.00 (s, 2H, OCH$_2$N); 5.10 (s, 2H, OCH$_2$N); 7.00 (d, 1H, phenyl); 7.14 (dd, 2H, phenyl); and 7.99 (d, 1H, phenyl).

Step B: 1,6-Dihydroxy-2,5-bis-(trans-2-methylcyclopentylaminomethyl)-naphthalene dihydrochloride; n.m.r data (200 MHz, CD$_3$OD): 1.10 (d, 6H, 2 CH$_3$'s); 4.44 (m, 2H, CH$_2$N); 4.72 (s, 2H, CH$_2$N); 7.22 (d, 1H, phenyl); 7.65 (dd, 2H, phenyl); and 8.32 (d, 1H, phenyl).

EXAMPLE 14

In Vivo Immunopotentiation Against Challenge with Lethal Doses of *Pseudomonas aeruginosa*

An immunocompromised mouse model, established by intraperitoneal treatment of random outbred albino CF1 female mice (ca. 25 g) with 250 mg/kg body weight of cyclophosphamide (CY) 4 days prior to bacterial challenge with *Pseudomonas aeruginosa*, was used as the assay system. In this model, test compounds were injected only once (2 hours) after CY treatment. After bacterial challenge, LD$_{50}$'s (50% lethal doses) were determined. Increased LD$_{50}$'s in treated mice over controls indicated a return to normality. The LD$_{50}$ for untreated or vehicle-treated mice was routinely $10^6$–$10^7$ colony forming units (CFU) of *P. aeruginosa* organisms. After CY treatment, the LD$_{50}$ was reduced to $10^1$ to $10^2$ CFU's. The protection afforded by test compound (Protective Index) was determined by calculating the number of LD$_{50}$'s of protection of treated animals over the LD$_{50}$ of CY controls. Results are given below:

| Experiment β | Test Compound | Relative No. LD$_{50}$'s |
|---|---|---|
| 1 | Example 2 | 320 |
| 2 | Example 3 | 2128 |
| 2 | Example 4 | 1000 |
| 3 | Example 5 | 133 |
| 3 | Example 6 | 151 |
| 4 | Example 7 | 1000 |

As is seen from the test results above, the compounds of the present invention provide for significant protection of the cyclophosphamide-immune compromised mouse against infection with a lethal challenge of *Pseudomonas aeruginosa*. Thus, for example, with the test compound of Example 4, the LD50 was raised by 1000-fold over untreated oontrols, indicating a return to the normal state for the host.

What is claimed is:

1. A method of enhancing host resistance against bacterial or fungal infection comprising administering to said host a compound of the formula:

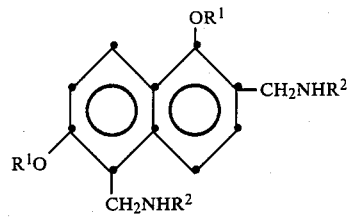

where R$^1$ is independently selected from H, C$_1$–C$_6$alkyl; R2 is independently selected from the group consisting of: 1-adamantylmethyl, 2-adamantylmethyl; 3-methyl-1-adamantylmethyl, 3-methyl-2-adamantylmethyl, 3,5-dimethyl-1-adamantylmethyl, 3-ethyl-1-adamantylmethyl, 3-propyl-1-adamantylmetyl, 3-methoxy-1-adamantylmethyl, 3-ethoxy-1-adamantylmethyl, cyclohexylmethyl-, 2-, 3-, 4-trimethyl-cyclohexylmethyl-, 2,4-dimethylcyclohexylmethyl-, 2-methoxycyclohexylmethyl-, 4-t-butoxycyclohexylmethyl-, 3-isopropoxycyclohexylmethyl-, tetrahydropyranyl-4-methyl, 2-methyletrahydropyranyl-4-methyl, 2,5-dimethoxytetrahydropyranyl-4-methyl, cyclopentylmethyl, methylcyclopentylmethyl tetrahydrosufyl unsubstituted or C1–C4 alkyl or alkoxy substituted monocycloalkyl, di- or tri- cycloalkyl, or heterocycloalkyl containing one oxygen hereto atom, and pharmaceutically acceptable acid addition salts thereof; in a physiologicaly acceptable medium in an amount effective to impart resistance against bacterial or fungal infection.

2. The method of claim 1 wherein R$^2$ is selected from unsubstituted or C$_1$–C$_4$ alkyl or alkoxy substituted adamantyl, cyclopentyl, cyclohexyl, cycloheptyl, or tetrahydropyranyl and cis or trans-isomers thereof.

3. The method of claim 1 wherein the compound is of the formula:

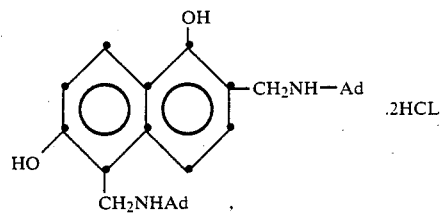

Where Ad is 1-adamantyl,

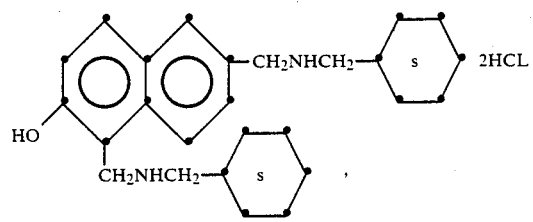

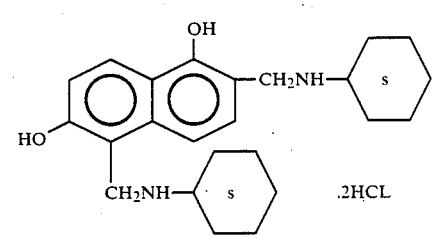

-continued
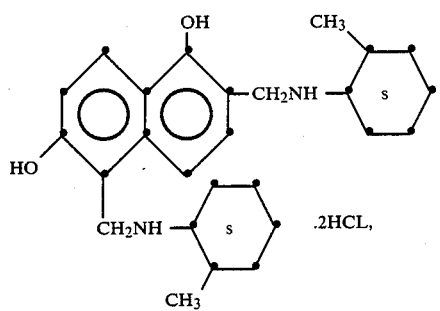
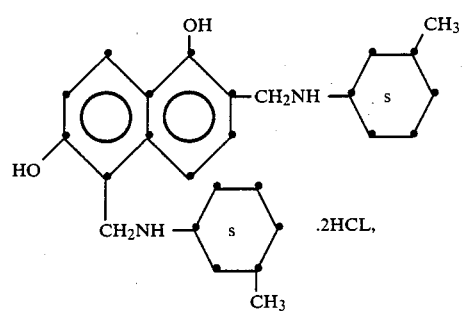
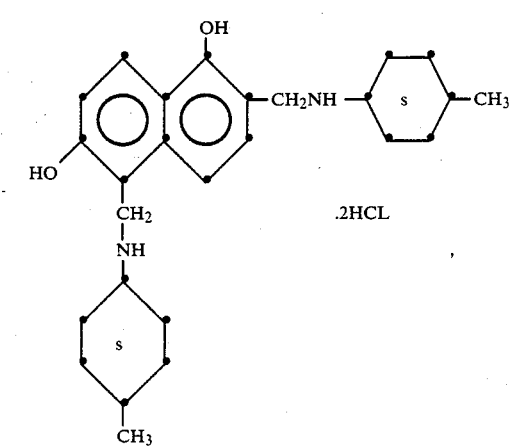
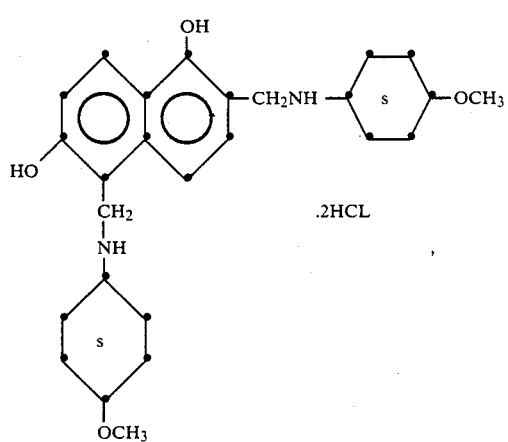
-continued
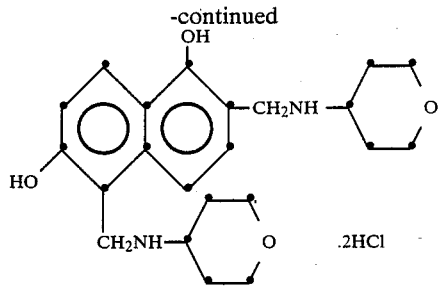
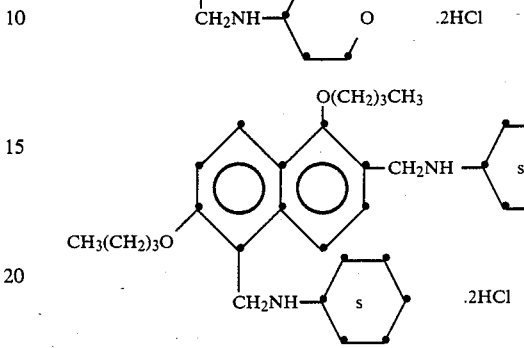
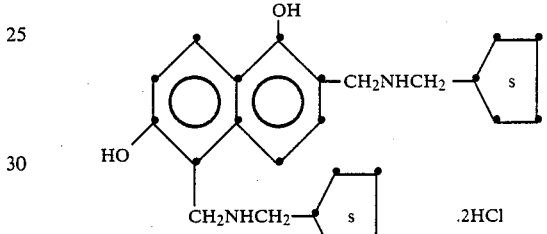
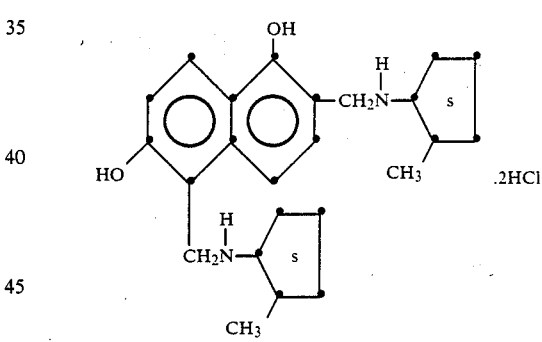
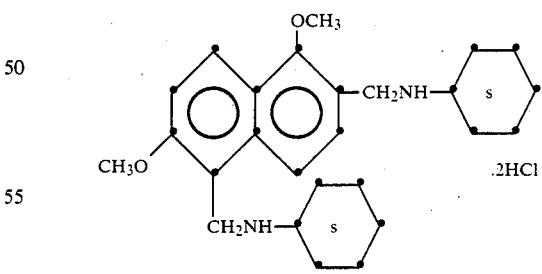
and cis, trans-isomers thereof.
4. The method of claim 1 wherein said heterocycloalkyl is selected from the group consisting of 4-tetrahydropyranyl-, 3-tetrahydropyranyl, 2-tetrahydropyranyl, 2-methyl-4-tetrahydropyranyl, 3-methyl-4-tetrahydropyranyl-, 2,5-dimethyltetrahydro-4-pyranyl, 2-methoxytetrahydro-4-pyranyl, and 2,6-dimethoxytetrahydro-4-pyranyl.
* * * * *